US00PP14173P29

(12) United States Plant Patent
Klemm

(10) Patent No.: US PP14,173 P2
(45) Date of Patent: Sep. 23, 2003

(54) CALIBRACHOA PLANT NAMED 'KLEC01056'

(75) Inventor: Nils Klemm, Stuttgart (DE)

(73) Assignee: Klemm + Sohn GmbH + Co. KG, Stuttgart (DE)

( * ) Notice: Subject to any disclaimer, the term of this patent is extended or adjusted under 35 U.S.C. 154(b) by 0 days.

(21) Appl. No.: 10/200,303

(22) Filed: Jul. 22, 2002

(51) Int. Cl.[7] ..... A01H 5/00
(52) U.S. Cl. ..... Plt./263
(58) Field of Search ..... Plt./263

*Primary Examiner*—Bruce R. Campell
*Assistant Examiner*—Annette H. Para
(74) *Attorney, Agent, or Firm*—C. A. Whealy

(57) ABSTRACT

A distinct cultivar of Calibrachoa plant named 'KLEC01056', characterized by its cascading plant habit; freely branching habit; early flowering habit; light yellow-colored flowers; and good weather tolerance.

1 Drawing Sheet

Botanical classification/cultivar designation: Calibrachoa sp. cultivar KLEC01056.

BACKGROUND OF THE INVENTION

The present Invention relates to a new and distinct cultivar of Calibrachoa plant, botanically known as Calibrachoa sp., and hereinafter referred to by the name 'KLEC01056'.

The new Calibrachoa is a product of a mutation induction breeding program conducted by the Inventor in Stuttgart, Germany. The objective of the program is to create new early-flowering Calibrachoa cultivars with compact and cascading growth habit, freely branching habit, and attractive flower colors.

The new cultivar originated by exposing unrooted cuttings of a proprietary selection of Calibrachoa identified as S 146, not patented, to X-ray radiation in Stuttgart, Germany. Terminal cuttings were harvested from the irradiated plants, planted and flowered in a controlled environment in Stuttgart, Germany. The new Calibrachoa was discovered and selected by the Inventor as a single flowering plant within this population in September, 1999.

Asexual reproduction of the new cultivar by terminal cuttings taken in a controlled environment in Stuttgart, Germany since September, 1999, has shown that the unique features of this new Calibrachoa are stable and reproduced true to type in successive generations.

SUMMARY OF THE INVENTION

Plants of the cultivar KLEC01056 have not been observed under all possible environmental conditions. The phenotype may vary somewhat with variations in environment such as temperature, light intensity, daylength, water status and fertility level without, however, any variance in genotype.

The following traits have been repeatedly observed and are determined to be the unique characteristics of 'KLEC01056'. These characteristics in combination distinguish 'KLEC01056' as a new and distinct cultivar of Calibrachoa:

1. Cascading plant habit.
2. Freely branching habit.
3. Early flowering habit.
4. Light yellow-colored flowers.

5. Good weather tolerance; tolerant to rain and low and high temperatures.

Plants of the new Calibrachoa differ primarily from plants of the parent selection primarily in flower color as plants of the selection S146 have white and red purple-colored flowers.

BRIEF DESCRIPTION OF THE PHOTOGRAPH

The accompanying colored photograph illustrates the overall appearance of the new cultivar, showing the colors as true as it is reasonably possible to obtain in colored reproductions of this type. Colors in the photograph may differ slightly from the color values cited in the detailed botanical description which accurately describe the colors of the new Calibrachoa. The photograph comprises a side perspective view of typical plants of 'KLEC01056' grown in a hanging basket container.

DETAILED BOTANICAL DESCRIPTION

In the following description, color references are made to The Royal Horticultural Society Colour Chart, 1995 Edition, except where general terms of ordinary dictionary significance are used. Plants grown in 12-cm containers were used for following description. Plants were grown under conditions which closely approximate commercial production conditions during the fall and winter in Stuttgart, Germany in glass-covered greenhouse. Plants used for the description and the photograph were about five months from planting rooted cuttings. During the production period, day and night temperatures ranged from 16 to 18° C. and light levels were about 20,000 lux.

Botanical classification: Calibrachoa sp. cultivar KLEC01056.

Parentage: Induced mutation of a proprietary selection of Calibrachoa sp. identified as S 146, not patented.

Propagation:

*Type cutting.*—Terminal vegetative cuttings.

*Time to initiate and develop roots.*—Summer: About 21 days at 20 to 26° C. Winter: About 28 days at 20° C.

*Root description.*—Numerous, fine, fibrous, well-branched, and white in color.

Plant description:

*Form.*—Annual flowering plant; initially upright to semi-upright then cascading; uniform flattened mounded appearance.

*Usage.*—Appropriate for hanging baskets, window boxes and patio containers.

*Plant height* (*from soil level to top of plant plane*).—About 12 cm.

*Plant diameter* (*area of spread*).—About 65 cm.

*Growth rate.*—Relatively moderate.

*Branching habit.*—Freely branching, about 6 lateral branches per plant; pinching is typically not required.

*Lateral branch description.*—Length: About 33 cm. Diameter: About 1 cm. Internode length: About 0.5 to 3.5 cm. Texture: Glabrous. Color: 145A.

*Foliage description.*—Leaves simple, generally symmetrical and long persisting; sessile. Arrangement: Alternate. Length: About 1 to 3 cm. Width: About 0.8 to 1.6 cm. Shape: Broadly elliptic. Apex: Broadly acute. Base: Attenuate. Margin: Entire. Texture, upper and lower surfaces: Smooth, glabrous. Venation pattern: Pinnate. Color: Young foliage, upper surface: 144A. Young foliage, lower surface: 143C. Fully expanded foliage, upper surface: 137B. Fully expanded foliage, lower surface: 137D. Venation, upper surface: 137B. Venation, lower surface: 144B.

Flower description:

*Flower type and habit.*—Flowers face somewhat upright or outward; single, axillary; salverform. Flowers not persistent. Freely flowering habit, about 12 to 15 open flowers and about 20 to 25 flower buds per lateral stem. Flowers not fragrant.

*Natural flowering season.*—Spring until frost in the autumn; flowering continuous.

*Time to flower.*—Early flowering; plants begin flowering about 12 weeks after planting.

*Flower longevity on the plant.*—About 6 to 7 days.

*Flower size.*—Diameter: About 2.5 cm. Tube length: About 1.3 cm. Throat diameter, distal end: About 7 mm. Tube diameter, proximal end: About 1 mm.

*Flower buds* (*before showing color*).—Length: About 1.4 cm. Diameter: About 4 mm. Shape: Roughly oblong. Color: 151A.

*Corolla.*—Arrangement/appearance: Single whorl of five petals, fused into flared trumpet. Petal length from throat: About 9 mm. Petal width: About 1 cm. Petal shape: Roughly spatulate with obtuse apex. Petal margin: Entire. Petal texture, upper and lower surfaces: Smooth, glabrous. Color: Petal, upper surface, when opening and fully opened: 2B; color changing to 1B with subsequent development; venation, 150A. Petal, lower surface, when opening and fully opened: 2C; venation, 150A. Flower throat (inside): 2B; venation, 150A. Flower tube (outside): 2B; venation, 150A.

*Sepals.*—Arrangement/appearance: Single whorl of five sepals, star-shaped. Length: About 1.2 cm. Width: About 5 mm. Shape: Elliptic. Apex: Acute. Margin: Entire. Texture, upper and lower surfaces: Smooth, glabrous. Color: Upper surface: 146A. Lower surface: 146B.

*Peduncles.*—Length: About 1.5 to 2 cm. Width: About 5 mm. Strength: Moderately strong. Angle: Erect to about 75° from vertical. Texture: Glabrous, smooth. Color: 143A.

*Reproductive organs.*—Stamens: Quantity: Five or six per flower. Anther shape: Elliptic. Anther length: About 1 to 2 mm. Anther color: 11B. Pollen amount: Scarce. Pollen color: 11B. Pistils: Quantity: One per flower. Pistil length: About 6 mm. Stigma shape: Oval. Stigma color: 149A. Style length: About 5 mm. Style color: 150A. Ovary color: 154A.

*Seed/fruit.*—Seed and fruit production has not been observed.

Disease/pest resistance: Plants of the new Calibrachoa have been noted to be resistant to Powdery Mildew. Plants of the new Calibrachoa have not been noted to be resistant to other pathogens and pests common to Calibrachoas.

Weather/temperature tolerance: Plants of the new Calibrachoa are tolerant to rain and wind and have been observed to tolerate temperatures from 1 to 50° C.

It is claimed:

1. A new and distinct cultivar of Calibrachoa plant named 'KLEC01056', as illustrated and described.

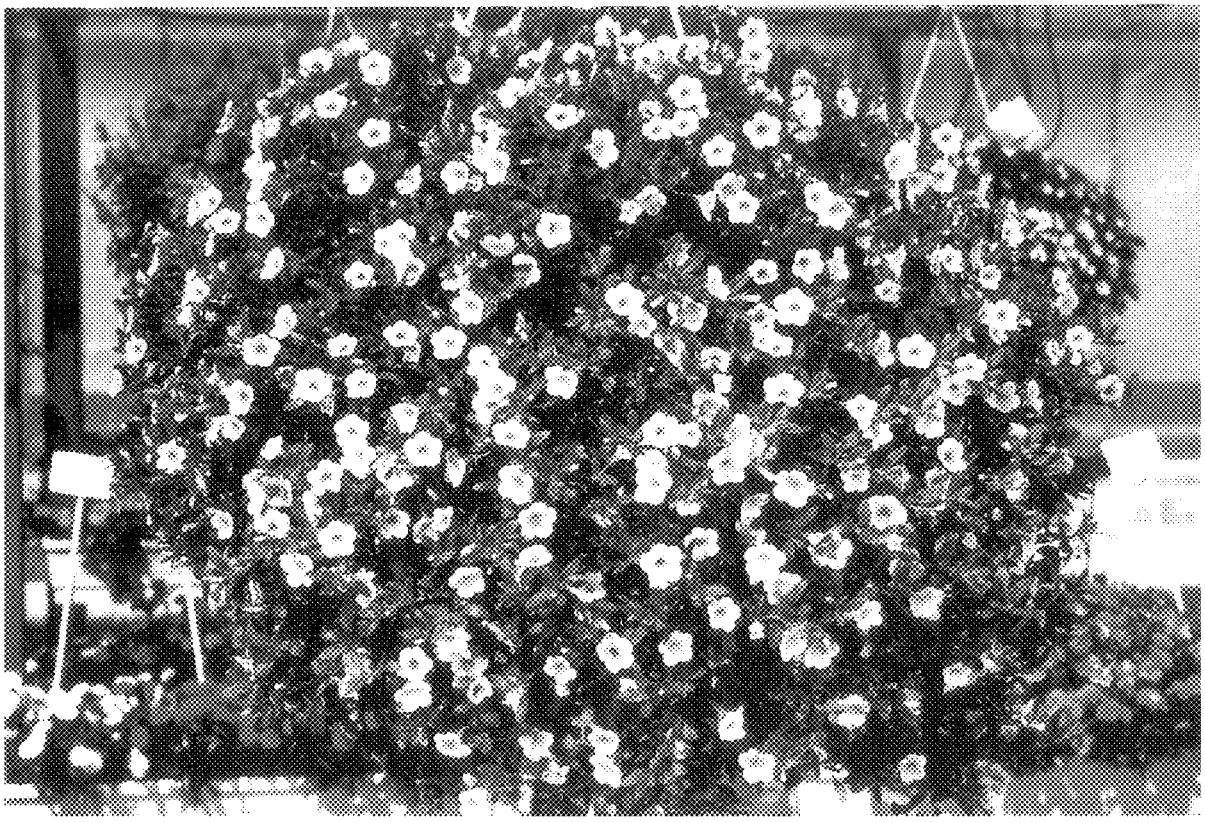

* * * * *